(12) United States Patent  
Nguyen et al.

(10) Patent No.: US 8,684,908 B2
(45) Date of Patent: Apr. 1, 2014

(54) CENTERING AID FOR IMPLANTABLE SLING

(75) Inventors: Steven Nguyen, North Brunswick, NJ (US); Katrin Elbert, Westfield, NJ (US); Daniel J. Smith, Dayton, NJ (US)

(73) Assignee: Ethicon, Inc., Somerville, NJ (US)

( * ) Notice: Subject to any disclaimer, the term of this patent is extended or adjusted under 35 U.S.C. 154(b) by 419 days.

(21) Appl. No.: 12/869,086

(22) Filed: Aug. 26, 2010

(65) Prior Publication Data

US 2012/0053398 A1    Mar. 1, 2012

(51) Int. Cl.
*A61F 2/02* (2006.01)
*A61B 17/08* (2006.01)

(52) U.S. Cl.
USPC ............ 600/30; 600/37; 606/151; 623/23.64

(58) Field of Classification Search
USPC ...................................... 600/30, 37; 606/151
See application file for complete search history.

(56) References Cited

U.S. PATENT DOCUMENTS

| | | | |
|---|---|---|---|
| 6,066,776 A | 5/2000 | Goodwin et al. | |
| 6,641,525 B2 | 11/2003 | Rocheleau et al. | |
| 6,648,921 B2 * | 11/2003 | Anderson et al. | 623/23.64 |
| 6,666,817 B2 | 12/2003 | Li | |
| 7,101,381 B2 | 9/2006 | Ford et al. | |
| 7,112,171 B2 | 9/2006 | Rocheleau et al. | |
| 7,235,043 B2 | 6/2007 | Gellman et al. | |
| 7,303,525 B2 * | 12/2007 | Watschke et al. | 600/30 |
| 7,402,133 B2 | 7/2008 | Chu et al. | |
| 7,601,118 B2 * | 10/2009 | Smith et al. | 600/30 |
| 7,951,066 B2 * | 5/2011 | Griffin et al. | 600/30 |
| 2002/0099258 A1 | 7/2002 | Staskin et al. | |
| 2003/0065402 A1 | 4/2003 | Anderson et al. | |
| 2003/0130670 A1 * | 7/2003 | Anderson et al. | 606/151 |
| 2004/0116944 A1 | 6/2004 | Chu et al. | |
| 2004/0225181 A1 * | 11/2004 | Chu et al. | 600/37 |
| 2005/0234291 A1 * | 10/2005 | Gingras | 600/30 |
| 2006/0199996 A1 | 9/2006 | Carabllo et al. | |
| 2007/0021649 A1 * | 1/2007 | Nowlin et al. | 600/30 |
| 2007/0299299 A1 | 12/2007 | Rosenblatt | |
| 2008/0021356 A1 | 1/2008 | Castello Escude et al. | |
| 2008/0125621 A1 * | 5/2008 | Gellman et al. | 600/37 |
| 2008/0139877 A1 | 6/2008 | Chu et al. | |

FOREIGN PATENT DOCUMENTS

| | | |
|---|---|---|
| EP | 1353601 B1 | 11/2005 |
| EP | 1342454 B1 | 5/2007 |
| EP | 1782759 A2 * | 5/2007 |
| EP | 1353598 B1 | 10/2007 |

OTHER PUBLICATIONS

Advantage® Transvaginal Mid-Urethral Sling System Brochure, Boston Scientific, available online Nov. 2008, copyright 2003.*
Kohli, N. et al., "A critical review of mid-urethral slings" Supplement to OBG Management, pp. 1-8 (2005).

* cited by examiner

*Primary Examiner* — Jacqueline Cheng
*Assistant Examiner* — Eileen Foley

(57) ABSTRACT

A surgical implant and method for its use. The surgical implant includes a biocompatible mesh having first and second ends, a length greater than a width, and a centering device including a solid, button-like element having opposing first and second surfaces and a peripheral outer edge extending therebetween. The centering device further includes a filamentary element having first and second ends fixedly secured to the peripheral edge of the button-like element so as to form a loop therebetween. The filamentary element is woven through the mesh at its longitudinal center in a direction perpendicular to the length of the mesh.

23 Claims, 3 Drawing Sheets

CENTERING AID FOR IMPLANTABLE SLING

BACKGROUND OF THE INVENTION

1. Field of the Invention

The present invention relates generally to surgical implants for treating incontinence or other surgical conditions, and more particularly, to centering aids used in conjunction with such implants to assist in proper placement of the implant.

2. Background Discussion

Female stress urinary incontinence (SUI) is a medical condition commonly associated with weakening of the pelvic muscles and/or connective tissues that support the urethra in its proper position. As a result, involuntary urine leakage occurs from simple physical activity, such as running or jumping, and even coughing or sneezing, as the urethra is not properly supported and does not remain fully closed during such activity.

A widely accepted medical procedure to correct SUI is the insertion of a tension-free, trans-vaginal tape that is surgically implanted in the pelvic tissue and that extends under and provides support for the urethra when pressure is exerted thereon. U.S. Pat. No. 5,899,909, the disclosure of which is incorporated herein by reference, describes in detail a typical procedure for treating SUI using a trans-vaginal tape. The tape is implanted by passing an elongated curved needle that is attached to one end of the tape through an incision in the vaginal wall, to one lateral side of the urethra, through the pelvic tissue behind the pubic bone, and exiting out through an incision made in the abdominal wall. The procedure is repeated for the other end of the mesh tape, this time on the other lateral side of the urethra, with the needle exiting through a second incision made in the abdominal wall of the patient. After the mesh tape is properly adjusted relative to the urethra, the free ends that extend outside of the abdominal wall are trimmed. Over time, fibroblasts grow into the mesh tape to anchor the tape in the surrounding tissue. Thus, the tape is left as an implant in the body to form an artificial ligament supporting the urethra in order to restore urinary continence. In another known method for implanting a trans-vaginal tape, the tape is inserted in a somewhat similar manner, but is brought out through the obturator foramen and exits the body through a small incision in each upper leg. Such a method is described in detail in U.S. Pat. No. 7,611,454 which is incorporated herein by reference in its entirety.

Following introduction of the trans-vaginal tapes described above, shorter length slings have been developed that do not require the entire tape to be passed out through secondary external incisions in the abdomen or upper leg, and that leave less foreign material behind within the body. One such device is described in detail in U.S. Pat. No. 7,601,118, which is incorporated herein by reference in its entirety. For these "mini" slings that do not exit the body, unless the mesh is properly centered there can be no guarantee that the respective ends of the sling extend far enough into the proper tissue, such as the obturator membranes, to ensure sufficient tissue ingrowth and resulting stabilization of the tape, as the ends of the tape are not visible to the surgeon.

To address this problem, some slings have been known to use a marker, such as a line or different color, at the mesh center as an indicator for proper positioning. Such a mark, however, is often difficult or impossible to see when the tape is deployed in the surgical incision due to the surrounding blood and tissue, particularly if it is moved slightly off center at any time.

Thus, there is a need for an improved implant including a device for assisting in its proper placement.

SUMMARY OF THE INVENTION

Provided herein is a surgical implant including a biocompatible mesh having first and second ends, a length greater than a width, and a centering device including a solid, button-like element having opposing first and second surfaces and a peripheral outer edge extending therebetween. The centering device further includes a filamentary element having first and second ends fixedly secured to the peripheral edge of the button-like element so as to form a loop therebetween. The filamentary element of the centering device is woven through the mesh at the longitudinal center thereof, and in a direction perpendicular to the length of the mesh.

The mesh of the implant may be made of a non-absorbable material, such as polypropylene, and may have a pore size of approximately 1-2 mm. Alternatively, the mesh may be made of an absorbable, or partially absorbable material. In one embodiment, the button-like element is made of polypropylene.

In yet another embodiment, the implant is a sling for treating stress urinary incontinence, and the mesh has a length of less than about 14 cm. The implant may further include second and third filamentary elements woven through first and second ends of the mesh respectively. In yet another embodiment, the implant further includes a first sheath portion enclosing a substantial portion of the first filamentary element and at least the first end of the mesh and a second sheath portion enclosing a substantial portion of the second filamentary element and at least the second end of the mesh. The first and second sheath portions may be made of polypropylene.

In yet another embodiment, at least one of said first and second surfaces has a central recess therein substantially surrounded by a raised peripheral edge.

Also provided is a method for treating stress urinary incontinence in a female patient, including the steps of obtaining a surgical implant including a biocompatible mesh having first and second ends and first and second filamentary elements extending from said first and second ends respectively, a length greater than a width, and a centering device including a solid, button-like element having opposing first and second surfaces and a peripheral outer edge extending therebetween. The centering device further includes a filamentary element having first and second ends fixedly secured to the peripheral edge of the button-like element so as to form a loop therebetween, and the filamentary element of the centering device is woven through the mesh at the longitudinal center thereof, and in a direction perpendicular to the length of the mesh. The method further includes making an incision in the vaginal wall of the patient, passing the implant through the incision, through a first pathway through the body on one lateral side of the urethra, and out of the first exterior incision in the patient's body such that the first filamentary element exits the patient's body and the first end of the mesh remains within the patient's body, passing the implant through the incision, through a second pathway through the body on the opposite lateral side of the urethra, and out through a second exterior of the patient's body such that the second filamentary element exits the patient's body and the second end of the mesh remains within the patient's body. The method further includes adjusting the implant to ensure that the centering device is substantially centered under the urethra, removing the first and second filamentary elements from the first and second respective ends of the mesh and from the body, cutting the filamentary element of the centering device and removing the centering device from the body, and leaving the mesh implanted within the body of the patient.

Also provided is a surgical implant assembly including a surgical implant having a biocompatible mesh having first and second ends and a length greater than a width, and a centering device including a solid, button-like element having opposing first and second surfaces and a peripheral outer edge extending therebetween. The centering device further includes a filamentary element having first and second ends fixedly secured to the peripheral edge of the button-like element so as to form a loop therebetween. The filamentary element of the centering device is woven through the mesh at the longitudinal center thereof, and in a direction perpendicular to the length of the mesh. The assembly further includes first and second introducers each having a handle, a needle element extending outwardly from the handle, and a tube element having a channel therein and a closed, tissue penetrating distal tip. The needle elements of the introducers are positioned within the channels of the respective tube elements, and proximal ends of the tube elements are coupled to first and second ends of the implant.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Although the present invention is described in detail in the context of implantable slings for urinary incontinence, the device and methods described herein have application to other surgical conditions where a centering aid on an implantable device is desired. For example, the centering aid described herein can be used in conjunction with an implantable mesh for treating various pelvic floor repair conditions.

Figure 1:
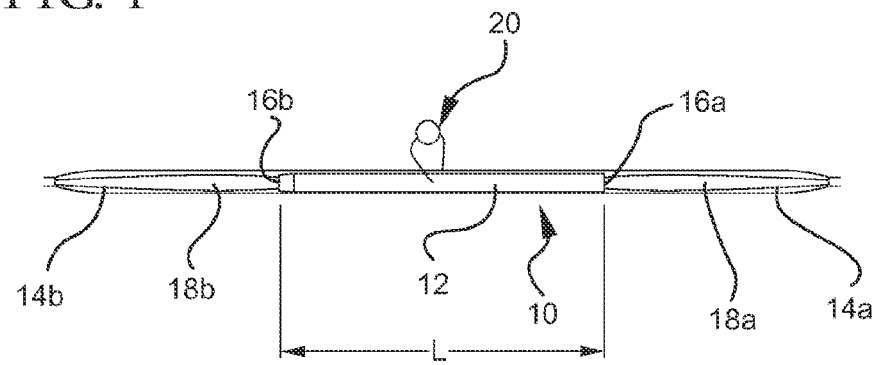
FIG. 1 illustrates an exemplary surgical implant incorporating a centering device according to the present invention.
Figure 2:
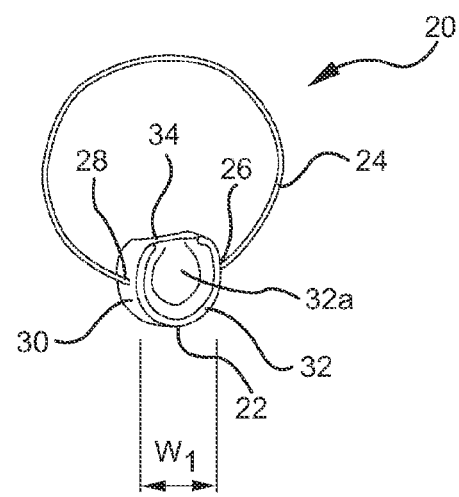
FIG. 2 illustrates in greater detail the centering device of the surgical implant of FIG. 1.
Figure 3:
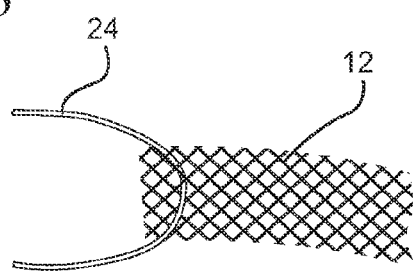
FIG. 3 is an enlarged view of FIG. 1 illustrating attachment of the centering device to the surgical implant.

Turning now to FIGS. 1-3, one embodiment of an implant 10 in the form of a sub-urethral tape particularly suited for the treatment of stress urinary incontinence (SUI) includes an implantable, elongated tape portion 12 designed to be placed beneath the urethra of a patient. In the illustrated embodiment, the tape portion is preferably 8-14 cm long, and includes one or more filamentary elements 14a, 14b extending outwardly from both sides. As will be described in further detail below, the filamentary elements have a length sufficient to extend from the first and second ends 16a, 16b of the tape portion 12 out through the body and out through first and second exterior incisions when implanted within a patient. Preferably, at least the first and second ends 16a, 16b of the tape and a length L of the filamentary elements 14a, 14b are enclosed within first and second sheath portions 18a, 18b to reduce friction and tissue drag and thereby facilitate implantation.

In a preferred embodiment, the tape portion may be formed as a mesh or netting with approximately 1 mm openings formed through the thickness thereof to allow fibroblasts to grow into the tape for securing the tape in the surrounding tissue of the patient. A suitable material for the tape is PROLENE®, which is a knitted or woven polypropylene mesh having a thickness of approximately 0.7 millimeters, and which is manufactured by Ethicon, Inc., Somerville, N.J. This material is approved by the FDA in the United States for implantation into the human body. Although PROLENE® is a preferred material, any suitable, bio-compatible material, absorbable, non-absorbable or a combination thereof, may also be used.

In one embodiment described in detail below that is particularly suitable for treatment of stress urinary incontinence in women has a width W of approximately 1.1 cm, and has a length $L_1$ between about 10 cm and about 14 cm, preferably 12 cm.

The implantable device 10 of FIG. 1 further includes a centering device 20 designed to aid the surgeon in proper positioning of the implant relative to the urethra during implantation. As shown in FIG. 2, the centering device 20 includes a button-like element 22 and a filamentary element 24. Although the "button-like" element of FIG. 2 is circular in-shape, any suitable shape or configuration may be used. The filamentary element 24 is threaded through the longitudinal center C-C of the tape portion as shown in FIG. 3, and is fixedly secured both at its first and second ends 26, 28 to the button-like element 22. As will be described further below, the filamentary element 24 is fixedly secured at both ends to the button-like element rather than slidably fixed or the like, so as to ensure the surgeon's ability to recapture the entire positioning device following its removal from the tape portion. The filamentary element may be comprised of any suitable, bio-compatible material, such as a size 2.0 PROLENE® suture, which is manufactured and sold by Ethicon, Inc. of Somerville, N.J. Any suitable fixation means may be used, such as ultrasonically welding, or mechanical means such as knotting, crimping, melting or the like.

The button-like element 22 has opposing first and second surfaces 32, 34 with a peripheral edge 30 extending therebetween. Although no necessary, one or both of the surfaces 32, 34 may have a central, recessed portion (i.e., 32a) surrounded by a raised, peripheral rim 32. The button-like element preferably has an overall width W1 of approximately 1 cm. The size of the button-like element (in combination with the recessed portion if present) is designed to accommodate a finger or thumb of a user so that the user may readily grasp the button-like element to thereby ensure proper placement and tensioning of the tape within the patient, and to ensure that it can readily be grasped for final removal. The button may be made of any suitable, bio-compatible material, such as polypropylene.

Figure 4:
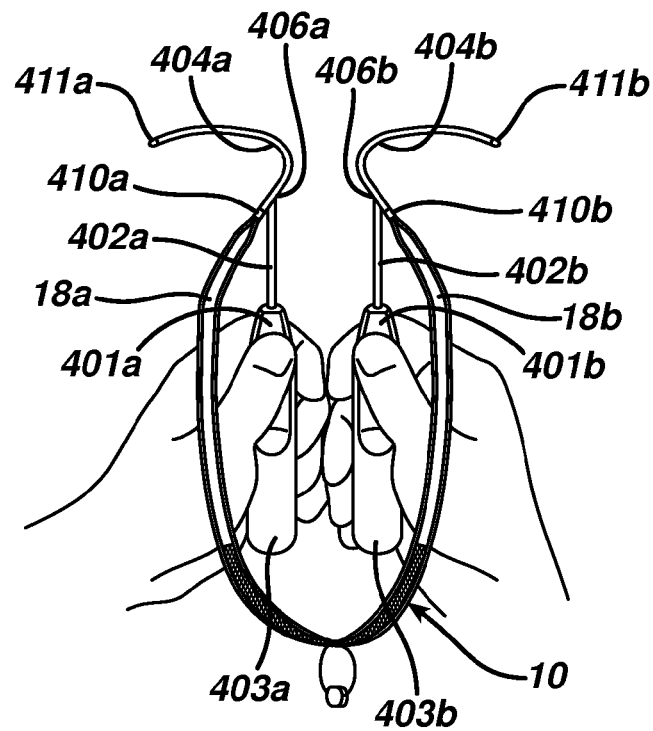
FIG. 4 illustrates the surgical implant of FIG. 1 in connection with one embodiment of an instrument assembly capable of being used to aid in implantation of the surgical implant.

Placement of the implant described above can be accomplished with any suitable surgical instrument. A preferred surgical instrument assembly is illustrated in FIG. 4. The surgical instrument assembly 400 includes first and second introducers 401a, 401b each having a needle element 402a, 402b and a handle portion 403a, 403b. The needle element extends outwardly from the handle to a distal end that is preferably blunt, and is somewhat helical in shape so as to easily pass around the ischio-pubic ramus to the exit point in the vicinity of the obturator foramen as will be described further below. First and second tube elements 404a, 404b each have a tissue penetrating distal end 411a, 411b and a channel extending from an opening 410a, 410b at the proximal end to the closed distal end. The proximal ends of the tube elements 404a, 404b are also fixedly coupled to the ends of the sheath elements 18a, 18b of the implant 10 by any suitable manner, such as by inserting the sheath elements into the proximal end opening of the respective tube elements.

The channel of the tube element has an inner diameter dimensioned to receive therein the needle elements 402a, 402b of the introducer 400. In a preferred embodiment, the needle elements are inserted into the channels through side apertures 406a, 406b. The outer diameter of the needle element is designed relative to the diameter of the channel of the tube element so that the surgical passer is readily insertable within the tube element, and removably therefrom with little frictional resistance. In this manner, following passage of the surgical implant through the body as described below, the introducer can readily be removed from the tube element without moving or otherwise disturbing the position of the sheath element and attached implant. In a preferred embodiment, the diameter of the needle element is approximately 3 mm and the inner diameter of the channel of the tube element is approximately 3.2 mm.

In a preferred embodiment, the tube element is made of a high-density polyethylene material.

One method for implanting a urethral sling such as the embodiment illustrated in FIG. 1 will now be described in detail in relation to FIGS. 5a-5c. The patient is first placed in the dorsal lithotomy position with the hips hyperflexed over the abdomen, and the bladder subsequently emptied. It may then be desirable to mark the exit points 501, 502 for the procedure by tracing a horizontal line 15a at the level of the urethral meatus, and a second line 15b parallel to and 2 cm above the first line. The exit points are marked on the second line 2 cm lateral to the folds of the thigh. A 1 cm mid-line incision 503 is then made in the vaginal mucosa, starting 1 cm proximal to the urethral meatus.

Following the initial incision, a blunt dissection is made toward, but not into, the obturator membrane. The path of the lateral dissection should be in the horizontal plane, and directed toward the ischio-pubic ramus in a 45 degree angle in relation to the coronal plane. The dissection should continue past the ischio-pubic ramus and into the obturator internus muscle, but should not perforate the obturator membrane.

Figure 5A:
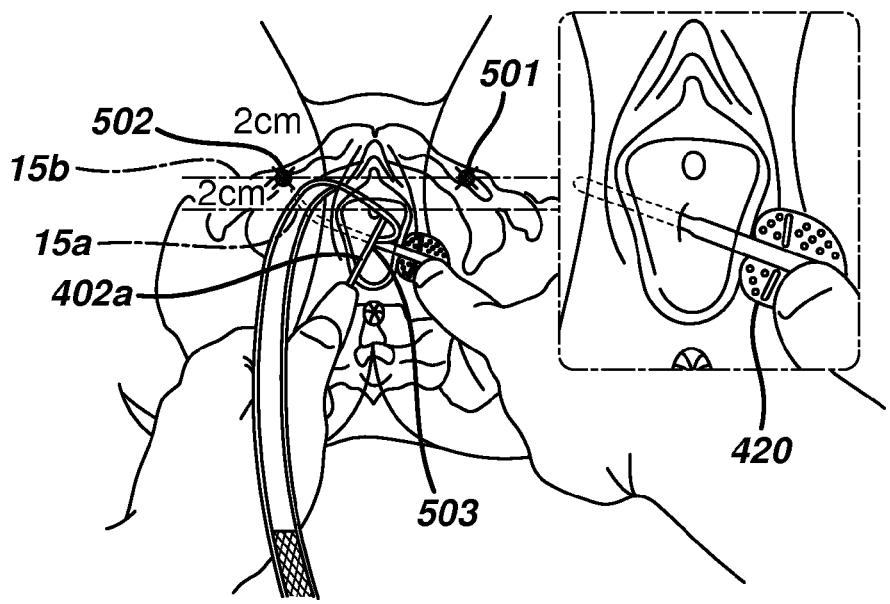
FIGS. 5a-5c illustrate various steps in an exemplary method for implanting a surgical implant such as that illustrated in FIG. 1.
Figure 5B:
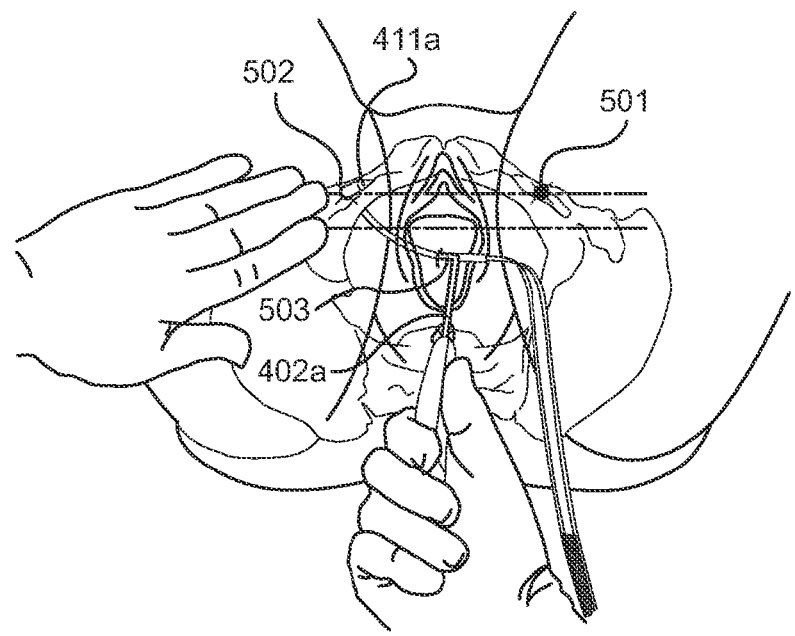
Figure 5C:
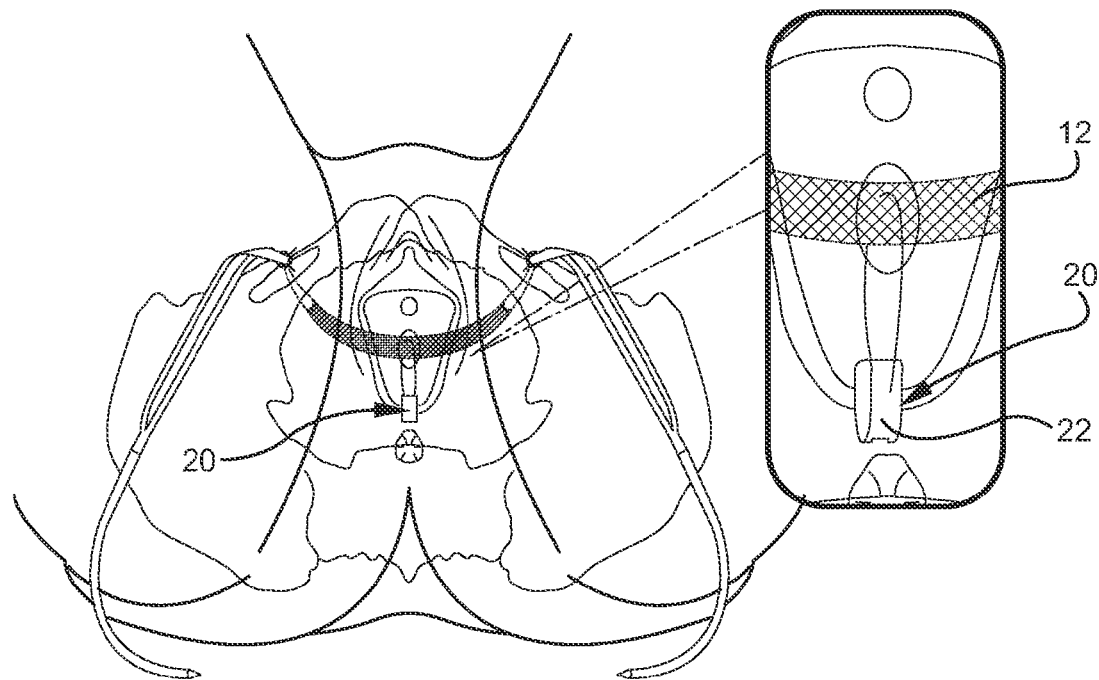

Using an insertion device such as that illustrated in FIG. 4, and preferably an additional guide 420 such as is shown in FIG. 5a, the guide is first inserted into the dissection tract, and one of the inserters and associated tube elements (coupled to the implant) is passed into the dissection tract along the guide until the distal tip 411a of the tube element is pushed slightly into the internus muscle but not into the obturator membrane. Once positioned in this manner, the tip 411a is then used to perforate the obturator membrane, the guide removed, and the introducer rotated tightly around the ischio-pubic ramus until the distal tip exits near or inferio-medial to the previously marked exit point 501. Once the tip exits the body, the tip is grabbed with a clamp or the like, and the needle element rotated back out of the body through the vaginal incision, leaving the tape and attached tube element in place.

The technique is repeated on the patient's other side so that the tape lies flat under the urethra. Following this initial placement, the tape should be further positioning by advancing both mesh sheaths until the positioning device 20 is central to the vaginal incision and the mesh is in contact with the urethra a shown in FIG. 5c. The mesh sheath is then cut in proximity to the exit points, and while maintaining suitable counter-traction on the mesh under the urethra, both sheaths are removed from the first and second ends of the tape by lateral pulling. The two sets of positioning lines 15a, 15b should remain in place. Following final placement, each of the positioning lines is removed by pulling on one end thereof, and the positioning device 20 is removed by cutting through the filament 24, grasping the button-like element 22, are removing it from the body.

During placement of the implant as described above, centering of the tape can be easily monitored, thereby ensuring that the ends of the tape extend at equal lengths into the tissue on both sides. The button-like element is designed so that it can be readily grasped by a user, and the length of the filamentary element 24 enables the button-like element to be positioned away from the incision so that it does not obscure view of the surgical field. The positioning device further allows for gentle testing of the tension of the tape following implantation. Finally, since only a filament is coupled to the tape, abrasion of the urethral tissue is minimized and removal of the positioned device is easily performed with virtually no risk of leaving anything behind in the body.

It will be apparent from the foregoing that, while particular forms of the is invention have been illustrated and described, various modifications can be made without departing from the spirit and scope of the invention. Accordingly, it is not intended that the invention be limited, except as by the appended claims.

What is claimed is:

1. A surgical implant comprising:
   a biocompatible mesh having first and second ends, and a length greater than a width; and
   a centering device including a solid, centering element having opposing first and second surfaces sized and shaped to accommodate a finger or thumb of a user to enable said user to grasp said centering element, and a peripheral outer edge extending therebetween, the centering device further including a filamentary element having first and second ends each fixedly secured to a respective portion of said peripheral edge of the centering element so as to form a loop therebetween and so as to not allow relative movement between the filamentary element and the centering element,
   wherein the filamentary element of the centering device is woven through the mesh only at a midpoint along the length of the mesh and in a direction perpendicular to the length of the mesh.

2. The surgical implant according to claim 1, wherein the mesh is comprised of a non-absorbable material.

3. The surgical implant according to claim 1, wherein the mesh is comprised of polypropylene and has a pore of approximately 1-2 mm.

4. The surgical implant according to claim 1, wherein the mesh is comprised of an absorbable, or partially absorbable material.

5. The surgical implant according to claim 1, wherein the centering element is comprised of polypropylene.

6. The surgical implant according to claim 1, wherein the implant is a sling for treating stress urinary incontinence, and the mesh has a length of less than about 14 cm.

7. The surgical implant according to claim 1, wherein the implant further comprises second and third filamentary elements woven through first and second ends of the mesh respectively.

8. The surgical implant according to claim 7, further comprising a first sheath portion enclosing a substantial portion of the second filamentary element and at least the first end of the mesh and a second sheath portion enclosing a substantial portion of the third filamentary element and at least the second end of the mesh.

9. The surgical implant according to claim 8, wherein the first and second sheath portions are comprised of polypropylene.

10. The surgical implant according to claim 1, wherein at least one of said first and second surfaces of the centering element has a central recess therein substantially surrounded by a raised peripheral edge.

11. A method for treating stress urinary incontinence in a female patient, comprising the steps of:
 obtaining a surgical implant including a biocompatible mesh having first and second ends and first and second filamentary elements extending from said first and second ends respectively, and a length greater than a width; and a centering device including a solid, centering element having opposing first and second surfaces sized and shaped to accommodate a finger or thumb of a user to enable said user to grasp said centering element, and a peripheral outer edge extending therebetween, the centering device further including a filamentary element having first and second ends each fixedly secured to a respective portion of said peripheral edge of the centering element so as to form a loop therebetween and so as to not allow relative movement between the filamentary element of the centering device and the centering element, wherein the filamentary element of the centering device is woven through the mesh only at a midpoint along the length of the mesh and in a direction perpendicular to the length of the mesh;
 making an incision in the vaginal wall of the patient;
 passing the implant through the incision, through a first pathway through the body on one lateral side of the urethra, and out of the a first exterior incision in said patient's body such that the first filamentary element exits the patient's body and the first end of the mesh remains within said patient's body;
body;
 passing the implant through the incision, through a second pathway through the body on the opposite lateral side of the urethra, and out through a second exterior of said patient's body such that the second filamentary element exits the patient's body and the second end of the mesh remains within said patient's body;
 adjusting the implant to ensure that the centering device is substantially centered under the urethra;
 removing the first and second filamentary elements from the first and second respective ends of the mesh and from the body;
 severing the filamentary element of the centering device and removing the centering device from the body; and
 leaving the mesh implanted within the body of the patient.

12. The method according to claim 11, wherein the implant further includes a first sheath portion enclosing a substantial portion of the first filamentary element and at least the first end of the mesh and a second sheath portion enclosing a substantial portion of the second filamentary element and at least the second end of the mesh, and method further comprising, following the passing steps, removing the first and second sheath portions from the body through the first and second exterior incisions.

13. The method according to claim 11, wherein the first and second passing steps are performed using one or more surgical instruments.

14. The method according to claim 11, wherein the mesh has a length of approximately 10-14 cm and a width of approximately 1-2 cm.

15. The method according to claim 14, wherein the mesh is comprised of a non-absorbable material.

16. The method according to claim 14, wherein the mesh is comprised of an absorbable or partially absorbable material.

17. The method according to claim 11, wherein at least one of said first and second surfaces of the centering element has a recess therein substantially surrounded by a raised peripheral edge.

18. A surgical implant assembly comprising:
 a surgical implant comprising a biocompatible mesh having first and second ends, and a length greater than a width, and a centering device including a solid, centering element having opposing first and second surfaces sized and shaped to accommodate a finger or thumb of a user to enable said user to grasp said centering element, and a peripheral outer edge extending therebetween, the centering device further including a filamentary element having first and second ends each fixedly secured to a respective portion of said peripheral edge of the buttonlike element so as to form a loop therebetween and so as to not allow for relative movement between filamentary element and the centering element, wherein the filamentary element of the centering device is woven through the mesh at the longitudinal center thereof, and in a direction perpendicular to the length of the mesh; and
 first and second introducers each having a handle, a needle element extending outwardly from the handle, and a tube element having a channel therein and a closed, tissue penetrating distal tip,
 wherein the needle elements of the introducers are removably positioned within the channels of the respective tube elements, and wherein proximal ends of the tube elements are coupled to first and second ends of the implant.

19. The surgical implant assembly according to claim 18, wherein the surgical implant further includes second and third filamentary elements woven through first and second ends of the mesh respectively.

20. The surgical implant assembly according to claim 18, wherein the surgical implant further comprises a first sheath portion enclosing a substantial portion of the second filamentary element and at least the first end of the mesh and a second sheath portion enclosing a substantial portion of the third filamentary element and at least the second end of the mesh.

21. The surgical implant assembly according to claim 20, wherein the first and second sheath portions are coupled to the proximal ends of the respective tube elements of the first and second introducers.

22. The surgical implant assembly according to claim 21, wherein the mesh is comprised of polypropylene.

23. The surgical implant assembly according to claim 18, wherein at least one of said first and second surfaces of the centering element has a central recess therein substantially surrounded by a raised peripheral edge.

* * * * *

UNITED STATES PATENT AND TRADEMARK OFFICE
CERTIFICATE OF CORRECTION

| | |
|---|---|
| PATENT NO. | : 8,684,908 B2 |
| APPLICATION NO. | : 12/869086 |
| DATED | : April 1, 2014 |
| INVENTOR(S) | : Nguyen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 557 days.

Signed and Sealed this
Twenty-first Day of July, 2015

Michelle K. Lee
*Director of the United States Patent and Trademark Office*